United States Patent [19]

Sasaki et al.

[11] Patent Number: 6,015,914
[45] Date of Patent: Jan. 18, 2000

[54] COMPOUND HAVING OXETANYL GROUP, PROCESS FOR PRODUCING SAME, AND CURING COMPOSITION

[75] Inventors: Hiroshi Sasaki; Akira Kuriyama, both of Aichi, Japan

[73] Assignee: Toagosei, Co., Ltd., Tokyo, Japan

[21] Appl. No.: 09/009,053

[22] Filed: Jan. 20, 1998

[30] Foreign Application Priority Data

Jan. 21, 1997 [JP] Japan ................................. 9-022053
Oct. 23, 1997 [JP] Japan ................................. 9-309431

[51] Int. Cl.⁷ .......................... C07D 305/00; C08G 59/68
[52] U.S. Cl. ........................ 549/510; 528/414; 528/416; 528/417
[58] Field of Search ........................... 549/510; 528/414, 528/416, 417

[56] References Cited

U.S. PATENT DOCUMENTS 5,463,084  10/1995  Crivello ................................. 549/214
5,663,289   9/1997  Archibald et al. ..................... 528/414

FOREIGN PATENT DOCUMENTS 58-11521A  1/1983  Japan .

*Primary Examiner*—John Kight
*Assistant Examiner*—Raymond Covington
*Attorney, Agent, or Firm*—Heslin & Rothenberg P.C.

[57] ABSTRACT

Provided is a compound having an oxetanyl group and represented by the following formula:

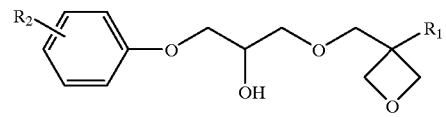

wherein $R_1$ represents a methyl group or an ethyl group and $R_2$ represents a hydrogen atom, a halogen atom, a straight or branched chain alkyl group of 1–5 carbon atoms, an unsubstituted or substituted phenyl group, an unsubstituted or substituted phenoxymethyl group, an unsubstituted or substituted phenoxypropyl group or an unsubstituted or substituted phenyl group. A process for producing the compound and a curing composition comprising the compound and a cationic polymerization initiator are also provided.

5 Claims, 2 Drawing Sheets

COMPOUND HAVING OXETANYL GROUP, PROCESS FOR PRODUCING SAME, AND CURING COMPOSITION

BACKGROUND OF THE INVENTION

The present invention relates to a compound having oxetanyl group which is utilizable for various reactions such as ring-opening polymerization and addition reaction, a process for producing the compound, and a curing composition comprising the compound. The compounds having oxetanyl group are useful in the fields of coating for wood, coating for metals and printing, for example, as ultraviolet-curing compositions which cure upon irradiation with ultraviolet rays.

The ultraviolet-curing of resins is utilized in the fields of coating for wood, coating for metals and printing taking advantage of high curing rate, good operability with requiring no solvents and very small energy quantity needed.

In the initial development in these fields, the research has been focused on ultraviolet ray-initiating radical polymerizable compounds such as polyfunctional acrylates and unsaturated polyesters, and, consequently, curing compositions comprising polyfunctional acrylates and unsaturated polyesters have been widely used.

Even at present, most of these researches are directed to ultraviolet ray-initiating radical polymerization, but it has been recognized that photo-initiating ionic polymerization is also fairly promising in many fields of application.

That is, since various monomers can be used in photo-initiation ionic polymerization, there is the possibility that cured products having various chemical and physical characteristics are obtained, and epoxy resins having an oxirane ring which are 3-membered cyclic ethers are investigated as the photo-initiation cationic polymerizable compounds. As a result, various curing compositions comprising epoxy resins are proposed. These photo-curing epoxy resins are excellent in properties such as adhesion, heat resistance and chemical resistance.

However, conventional photo-curing epoxy resins have the problem of low photo-curing rate. Therefore, they cannot be used for the uses such as coating for paper and plastics which requires rapid photo-curing. Accordingly, it is earnestly desired to improve curing rate with taking advantage of the characteristics of epoxy resins.

On the other hand, it is reported that polyfunctional oxetane monomers having a plurality of oxetanyl groups in one molecule which are 4-membered cyclic ethers have photo-curability equal to or higher than the corresponding polyfunctional epoxides ("Journal of Macromolecule Science", Vol. A29, No. 10, Page 915, 1992; Vol. A30, Nos. 2 & 3, Page 173, 1993; Vol. A30, Nos. 2 & 3, Page 189, 1993). Furthermore, photo-curing compositions mainly composed of polyfunctional oxetane monomers are also proposed (JP-A-6-16804).

Ultraviolet-curing resins obtained using these polyfunctional oxetane monomers have the characteristic that ultraviolet-curing rate thereof is much higher than that of epoxy resins.

However, although high curing rate is an important feature in photo-curing resins, it is also necessary that properties of cured products are superior. Photo-curing resins using oxetane compounds which have been hitherto reported are inferior in properties of the coat after cured to those mainly composed of epoxy resins. Therefore, photo-curing resins having oxetanyl groups as polymerizable groups have a rapid photo-curability, but can hardly be applied to the uses which require characteristics such as adhesion and elongation.

SUMMARY OF THE INVENTION

The object of the present invention is to provide compounds having an oxetanyl group which have rapid curability upon irradiation with light for a short time and which can give cured products excellent in various characteristics such as adhesion and elongation when they are used for ultraviolet-curing resins, a process for producing the compounds, and curing compositions.

As a result of intensive research, the inventors have found that compounds of a specific structure having oxetanyl group, especially, two oxetanyl groups in one molecule can solve the above problems, and, furthermore, they have found an industrially advantageous process for producing the compounds. Thus, the present invention has been accomplished.

That is, first, the present invention relates to compounds having an oxetanyl group and represented by the following formula (1), and especially to compounds having an oxetanyl group represented by the following formula (2) or (3).

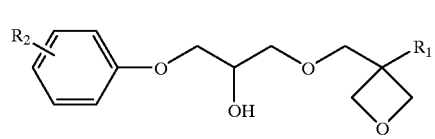

(1)

wherein $R_1$ represents a methyl group or an ethyl group and $R_2$ represents a hydrogen atom, a halogen atom, a straight or branched chain alkyl group of 1–5 carbon atoms, an unsubstituted or substituted phenyl group, an unsubstituted or substituted phenoxymethyl group, an unsubstituted or substituted phenoxypropyl group or an unsubstituted or substituted phenylalkyl group.

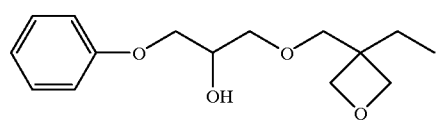

(2)

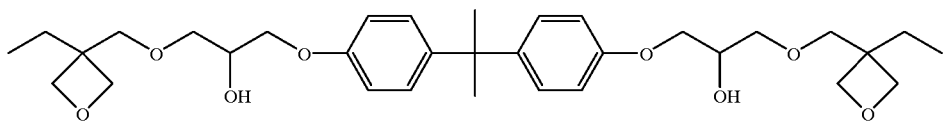

(3)

Secondarily, the present invention relates to a process for producing the above compounds having an oxetanyl group which comprises reacting 3-[(oxiranylmethoxy)methyl]oxetane represented by the following formula (4) with a phenol in the presence of an alkali metal hydroxide.

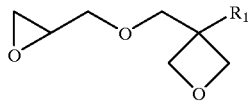

(4)

wherein $R_1$ represents a methyl group or an ethyl group.

Thirdly, the present invention relates to curing compositions comprising the above compound having an oxetanyl group and a cationic polymerization initiator.

DETAILED DESCRIPTION OF THE INVENTION

Figure 1:
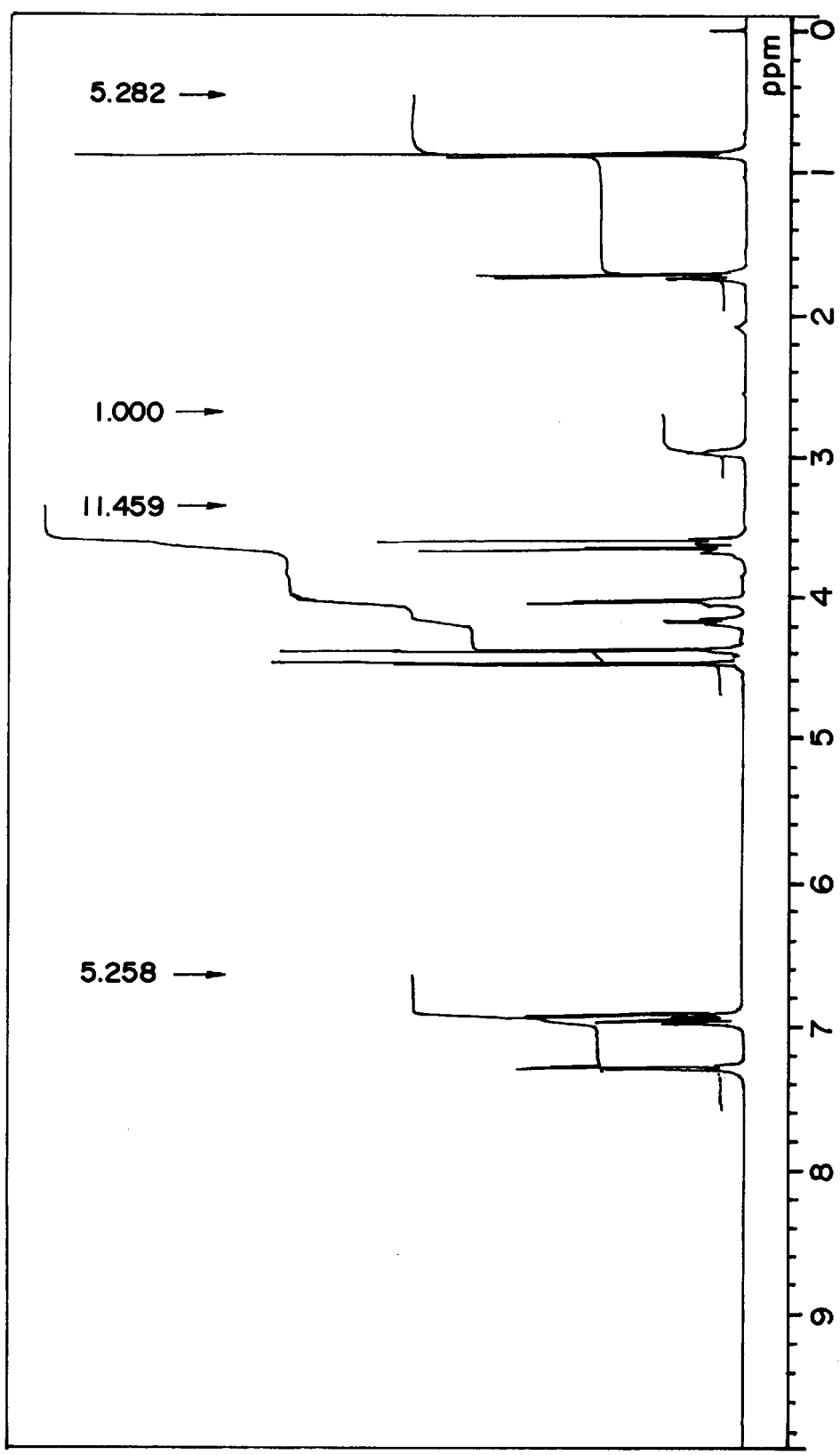
FIG. 1 shows a $^1$H-NMR spectrum of the compound 1 prepared in Example 1.

The present invention will be explained in detail.

1) Compounds having an oxetanyl group:

The compounds having oxetanyl group according to the present invention are those which are represented by the above formula (1), and preferred are those which are represented by the following formula (5).

oxetanyl group is a compound represented by the above formula (4) and this compound can be produced in high yields, for example, by the reaction of 3-hydroxymethyloxetane represented by the following formula (6) with epichlorohydrine.

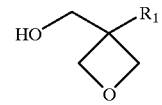

(6)

wherein $R_1$ represents a methyl group or an ethyl group.

The phenol which is another starting material is a phenol or substitued phenol represented by the following formula (7).

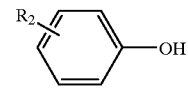

(7)

wherein $R_2$ represents a hydrogen atom, a halogen atom, a straight or branched chain alkyl group of 1–5 carbon atoms, an unsubstituted or substituted phenyl group, an unsubstituted or substituted phenoxymethyl group, an unsubstituted or substituted phenoxypropyl group or an unsubstituted or substituted phenylalkyl group.

The reaction between 3-[(oxiranylmethoxy)methyl]oxetane and phenol is carried out by employing conditions of addition reaction conducted in the field of usual organic synthesis. The proportion of 3-[(oxiranylmethoxy)methyl]

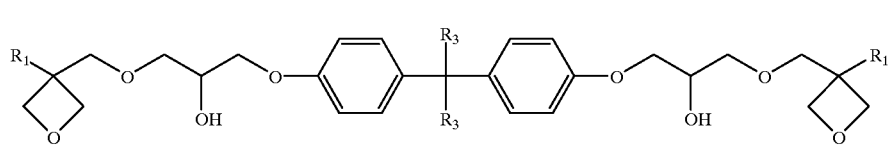

(5)

In the formula (5), $R_1$ represents a methyl group or an ethyl group and $R_3$ represents a hydrogen atom, a halogen atom, a methyl group, a phenyl group or a trihalogenomethyl group. Of these compounds, those compounds in which $R_3$ is methyl group are especially preferred because starting materials are easily available and cured products have moderate flexibility and rigidity.

2) Process for producing the compounds having oxetanyl group:

The compounds having oxetanyl group of the present invention can be produced, for example, by addition reaction of the above-mentioned 3-[(oxiranylmethoxy)methyl]oxetane with a phenol in the presence of an alkali metal hydroxide.

3-[(Oxiranylmethoxy)methyl]oxetane which is one of starting materials for producing the compounds having oxetane and phenol in the reaction is suitably 0.5–1.5 mol of phenol for 1.0 mol of 3-[(oxiranylmethoxy)methyl]oxetane.

Furthermore, the reaction is preferably carried out in the presence of an alkali metal hydroxide, and the other reaction conditions are not especially limited, and there may be employed the conditions similar to those for the known addition reactions of compounds having a phenolic hydroxyl group to epoxy compounds which are carried out in the presence of alkali metal hydroxides.

The alkali metal hydroxides are not particularly limited as far as they are hydroxides of alkali metals, but sodium hydroxide and potassium hydroxide are preferred from the points of reactivity and easiness in availability. Amount of the alkali metal hydroxides used is suitably 0.01–0.3 mol for 1 mol of the phenol.

The above reaction proceeds either in the presence or absence of organic solvents, but preferably the reaction is carried out in the absence of solvents because the reaction rate is higher. Organic solvents used are not limited as far as reaction temperature can be maintained, but toluene and xylene are preferred.

Suitable reaction temperature for preferable reaction is in the range of 100–200° C., and especially preferable temperature is 120–150° C. Reaction time can be optionally selected depending on the reaction temperature, and is preferably 1–20 hours.

After completion of the reaction, the reaction products are desirably subjected to extraction, separation and concentration generally employed in the reactions of organic compounds and further purified by distillation and chromatography.

3) Active energy ray-curing compositions:

The compounds having oxetanyl group of the present invention can be used satisfactorily for various uses as curing compositions by adding thereto cationic polymerization initiators such as compounds initiating cationic polymerization upon irradiation with active energy rays (hereinafter referred to as "cationic photopolymerization initiator").

Compounds which initiate cationic polymerization upon irradiation with active energy rays include known various cationic photopolymerization initiators. Among them, preferred are onium salts such as diaryliodonium salts and triarylsulfonium salts represented by the following formula (8).

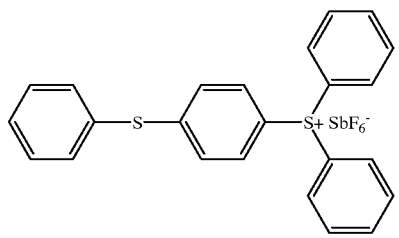

(8)

Amount of the cationic photopolymerization initiators is preferably 0.1–10 parts by weight, especially preferably 0.5–5 parts by weight for 100 parts by weight of the compound having oxetanyl group.

The compound having oxetanyl group and the cationic photopolymerization initiator can be mixed by conventional methods.

The curing compositions of the present invention can contain inorganic fillers, dyes, pigments, viscosity modifiers, treating agents, ultraviolet screening agents, etc. in addition to the above-mentioned essential components.

Furthermore, the curing compositions of the present invention preferably contain alicyclic epoxy compounds represented by the following formula (9) and oxetane compounds represented by the following formula (10) in order to improve curability upon irradiation with light. Amount of these compounds used is preferably 1–95 parts by weight, especially preferably 5–90 parts by weight for 100 parts by weight of the compound having oxetanyl group.

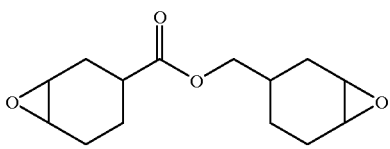

(9)

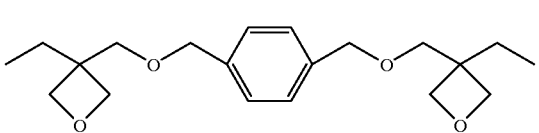

(10)

The curing composition of the present invention can be easily cured by irradiation with active energy rays such as ultraviolet rays. Various light sources can be utilized, such as, for example, mercury arc lamp, xenon arc lamp and sunlight as ultraviolet rays. In this case, intensity of irradiation for substrate is preferably 0.01 $W/cm^2$ or more, and curing of the composition is preferably carried out continuously in 1–20 seconds.

The curing compositions of the present invention can be applied to substrates such as metals, rubbers, plastics, films, papers, woods and ceramics. Uses of the compositions are, for example, coating compositions for plastics, metals and papers, luster varnishes, protective, decorative and insulation coatings, coating compositions for optical fibers, printing inks, sealants, adhesives, photoresists, laminates and printing plates.

The present invention will be explained in more detail by the following examples.

EXAMPLE 1

3-Ethyl-3-[(oxiranylmethoxy)methyl]oxetane (172.2 g, 1.0 mol), phenol (94.1 g, 1.0 mol) and potassium hydroxide (1.7 g, 0.03 mol) were charged in a glass flask of 2000 ml, and reaction was carried out at 130° C. for 3 hours with stirring by a magnetic stirrer. After completion of the reaction, toluene (300 ml) and water (500 ml) were added, followed by separating into an organic layer and an aqueous layer by a separating funnel. The separated organic layer was washed twice with water. After toluene was distilled off, the residue was subjected to distillation to obtain compound 1 represented by the following formula (231.6 g, yield 87 mol %). The compound 1 had a boiling point of 175° C. (0.8 mmHg), and structure of the compound was confirmed by $^1$H-NMR spectrum shown in FIG. 1.

EXAMPLE 2

Example 1 was repeated, except that 300 ml of toluene was used as organic solvent and the reaction time was 8 hours, thereby to obtain compound 1 at a yield of 85 mol %.

EXAMPLE 3

Example 1 was repeated, except that p-t-butylphenol (150.2 g, 1.0 mol) was used in place of phenol. Since distillation was difficult to perform, only toluene was distilled off to nearly quantitatively obtain compound 2 represented by the following formula.

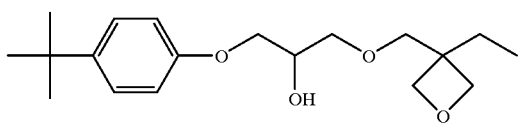

EXAMPLE 4

Example 1 was repeated, except that p-(2-phenyl-isopropyl)phenol (212.3 g, 1.0 mol) was used in place of phenol. Since distillation was difficult to perform, only toluene was distilled off to nearly quantitatively obtain compound 3 represented by the following formula.

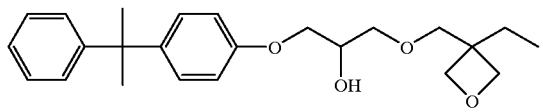

EXAMPLES 5–9 AND COMPARATIVE EXAMPLE 1

Compounds 1–3 obtained in Examples 1, 3 and 4, a bifunctional oxetane compound represented by the above formula (10) and a photoinitiator UV-1699 (manufactured by Union Carbide Corporation) were mixed at the ratio as shown in Table 1, and adhesion test was conducted under the following conditions. The results are shown in Table 1.

1) Ultraviolet curing conditions: The composition was irradiated with ultraviolet rays by an ultraviolet lamp (H bulb) manufactured by Fusion Inc. (integral quantity of light: 2 J/cm$^2$).

2) Adhesion evaluation: The composition was coated at a thickness of 10μ on a steel sheet by a bar coater and cured under the above conditions. The adhesion was evaluated by cross-hatch adhesion test.

O: No peeling occurred.

Δ: Partial peeling occurred.

X: Overall peeling occurred.

TABLE 1

| | Example | | | | Comparative example |
|---|---|---|---|---|---|
| | 5 | 6 | 7 | 8 | 1 |
| Mixing ratio (% by weight) | | | | | |
| Compound 1 | 20 | 40 | | | |
| Compound 2 | | | 40 | | |
| Compound 3 | | | | 40 | |
| Bifunctional oxetane compound | 75 | 55 | 55 | 55 | 95 |
| Photoininiator | 5 | 5 | 5 | 5 | 5 |
| Adhesion test | 0 | 0 | 0 | 0 | Δ |

EXAMPLE 9

Figure 2:
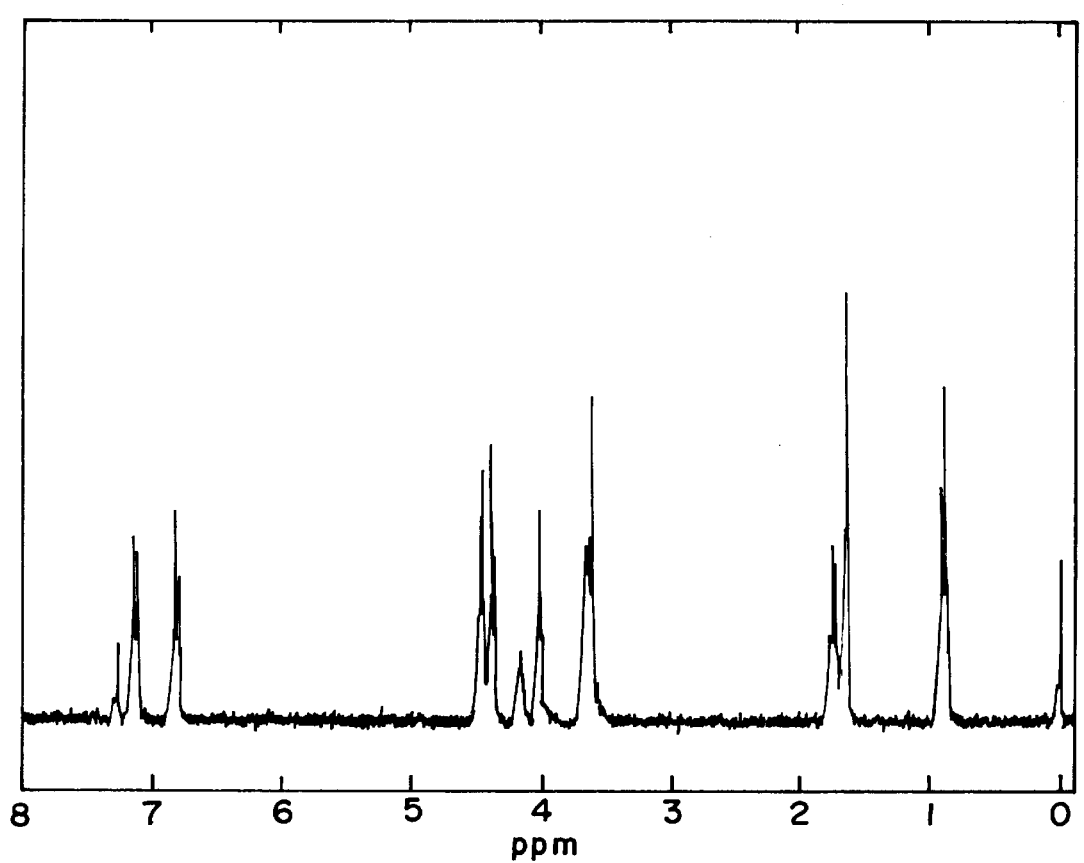
FIG. 2 shows a $^1$H-NMR spectrum of the compound 4 prepared in Example 9.

3-Ethyl-3-[(oxiranylmethoxy)methyl]oxetane (172.2 g, 1.0 mol), bisphenol A (114.2 g, 0.5 mol) and potassium hydroxide (3.3 g, 0.05 mol) were charged in a glass flask, and reaction was carried out at 130° C. for 3 hours with stirring by a magnetic stirrer. After completion of the reaction, toluene (300 ml) and water (500 ml) were added, followed by separating an organic layer by a separating funnel. The separated organic layer was washed twice with water, and then toluene was distilled off to nearly quantitatively obtain compound 4. It was confirmed by $^1$H-NMR spectrum shown in FIG. 2 that the compound 4 had the following structure.

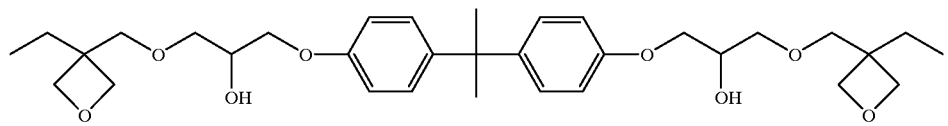

EXAMPLE 10

Example 9 was repeated, except that toluene (300 ml) was added as an organic solvent and the reaction time was 8 hours, thereby to obtain compound 4 as in Example 9.

EXAMPLES 11–16 AND COMPARATIVE EXAMPLES 2–4

Compound 4 obtained in Example 9, a bifunctional epoxy compound represented by the above formula (9), a bifunctional oxetane compound represented by the above formula (10) and a photoinitiator (UVI-6990 manufactured by Union Carbide Corporation) were mixed at the ratio as shown in Table 2, and evaluation of the resulting compositions was conducted on curability and adhesion under the following conditions. The results are shown in Table 2. Furthermore, compositions of comparative example containing no compound 4 and results of the evaluation are also shown in Table 2.

(Curability and adhesion tests)

Ultraviolet irradiation conditions: The composition was cured by irradiation with ultraviolet rays by an ultraviolet lamp (H bulb) manufactured by Fusion Inc.

Conditions for evaluation of curability: The composition was coated at a thickness of 10 p on an aluminum sheet by a bar coater and curing was confirmed by touching with finger. Curability was evaluated in terms of curing time (second).

Conditions for evaluation of adhesion: The composition was coated at a thickness of 10μ on an aluminum sheet by a bar coater and cured with an integral quantity of light of 500 ml/cm². The adhesion was evaluated by cross-hatch adhesion test. The numerical value in Table 2 shows the number of residual squares per 100 squares.

TABLE 2

| | Mixing ratio (Part by weight) | | | Properties | |
|---|---|---|---|---|---|
| | Compound 4 | Epoxy compound | Oxetane compound | Photo-initiator | Curability | Adhesion |

| Example | | | | | | |
|---|---|---|---|---|---|---|
| 11 | 97 | | | 3 | <1 sec. | 100/100 |
| 12 | 20 | 77 | | 3 | 3 sec. | 100/100 |
| 13 | 30 | 67 | | 3 | <1 sec. | 100/100 |
| 14 | 40 | 57 | | 3 | <1 sec. | 100/100 |
| 15 | 57 | | 40 | 3 | <1 sec. | 100/100 |
| 16 | 30 | 57 | 10 | 3 | <1 sec. | 100/100 |
| Comparative Example | | | | | | |
| 2 | | 97 | | 3 | 5 sec. | 100/100 |
| 3 | | 67 | 30 | 3 | 4 sec. | 70/100 |
| 4 | | 57 | 40 | 3 | 2 sec. | 30/100 |

The compounds having an oxetanyl group of the present invention rapidly cure upon irradiation with light for a short time. The cured products are superior in adhesion and elongation. Thus, the compounds are useful in the fields of coating for wood, coating for metals and printing. Moreover, according to the production process of the present invention, the compounds can be produced by industrially superior process.

Furthermore, the active energy ray-curing compositions comprising the compounds having an oxetanyl group of the present invention can form a coat excellent in curability and adhesion and can be utilized for various industrial uses.

What is claimed is:

1. A compound having an oxetanyl group and represented by the following formula:

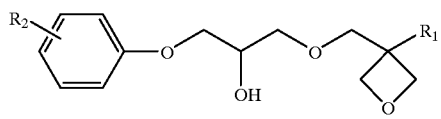

wherein $R_1$ represents a methyl group or an ethyl group and $R_2$ represents a hydrogen atom, a halogen atom, a straight or branched chain alkyl group of 1–5 carbon atoms, an unsubstituted or substituted phenyl group, an unsubstituted or substituted phenoxymethyl group, an unsubstituted or substituted phenoxypropyl group or an unsubstituted or substituted phenylalkyl group.

2. A compound having an oxetanyl group and represented by the following formula:

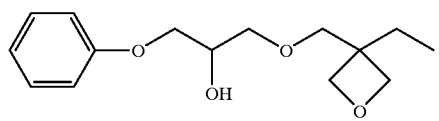

3. A compound having an oxetanyl group and represented by the following formula:

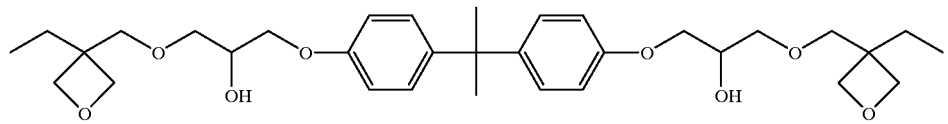

4. A process for producing the compound having an oxetanyl group of claim 1 which comprises reacting a 3-[(oxiranylmethoxy)methyl]oxetane represented by the following formula with a phenol in the presence of an alkali metal hydroxide:

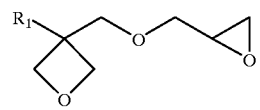

wherein $R_1$ represents a methyl group or an ethyl group.

5. A curing composition comprising (a) a cationic polymerization initiator and (b) a compound of formula

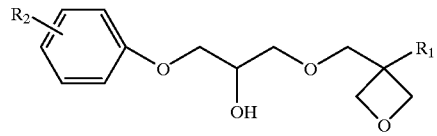

wherein:
  $R^1$ is chosen from a methyl group and an ethyl group; and
  $R^2$ is chosen from a hydrogen atom, a halogen atom, a straight or branched chain alkyl group of 1–5 carbon atoms, an unsubstituted or substituted phenyl group, an unsubstituted or substituted phenoxymethyl group, an unsubstituted or substituted phenoxypropyl group and an unsubstituted or substituted phenylalkyl group.

* * * * *